(12) United States Patent
Owens et al.

(10) Patent No.: US 7,751,989 B2
(45) Date of Patent: Jul. 6, 2010

(54) GUIDED WAVE PIPELINE INSPECTION SYSTEM WITH ENHANCED FOCUSING CAPABILITY

(75) Inventors: Steven E. Owens, Bellefonte, PA (US); Joseph L. Rose, State College, PA (US); Jason K. Van Velsor, State College, PA (US); Li Zhang, State College, PA (US); Michael J. Avioli, Havertown, PA (US)

(73) Assignee: FBS, Inc., State College, PA (US)

( * ) Notice: Subject to any disclaimer, the term of this patent is extended or adjusted under 35 U.S.C. 154(b) by 203 days.

(21) Appl. No.: 11/948,383

(22) Filed: Nov. 30, 2007

(65) Prior Publication Data

US 2008/0133200 A1     Jun. 5, 2008

Related U.S. Application Data

(60) Provisional application No. 60/867,976, filed on Nov. 30, 2006.

(51) Int. Cl.
     *G06F 17/50*      (2006.01)
     *G01N 29/44*      (2006.01)
     *H04L 12/26*      (2006.01)

(52) U.S. Cl. .............................. 702/33; 702/34; 702/35; 702/36; 702/37; 702/38; 702/39; 702/40; 73/622; 73/623; 73/624; 73/625; 73/626; 73/627; 73/628; 73/640; 73/641; 703/13; 370/241

(58) Field of Classification Search ............. 702/33–40; 73/622–628, 640–641; 703/13; 370/241
See application file for complete search history.

(56) References Cited

U.S. PATENT DOCUMENTS 4,909,091 A *   3/1990   Ellmann et al. ............ 73/866.5
5,590,659 A *   1/1997   Hamilton et al. ............ 600/447

OTHER PUBLICATIONS

Sun, Z. et al., "Flexural Torsional Guided Wave Mechanics and Focusing in Pipe", Journal of Pressure Vessel Technology, 2005, 127:471-478.
Li, J. et al., "Angular-Profile Tuning of Guided Waves in Hollow Cylinders Using a Circumferential Phased Array", IEEE Transactions on Ultrasonics, Ferroelectrics, and Frequency Control, 202, 19(12):1720-1729.

(Continued)

*Primary Examiner*—Sujoy K Kundu
(74) *Attorney, Agent, or Firm*—Duane Morris LLP (57) ABSTRACT

A system for inspecting a pipeline having at least two transducers divided into segments, the segments each containing a number of sensors, wherein a maximum number of segments is equal to a number of transducers, an arrangement configured to send, receive and store signals, wherein the arrangement has a number of pulser channels and a number of receiver channels, wherein the arrangement has at least one multiplexing arrangement for multiplexing signals from the arrangement; and a time delay arrangement connected to the arrangement configured to send, receive and store signals. The system may also provide for focal point skewing, near real time coating compensation for proper excitation mode, adjusted time delay capability and the ability to focus beyond changes in geometry.

14 Claims, 5 Drawing Sheets

OTHER PUBLICATIONS

Rose, J.L. et al., "A Guided Wave Inspection Technique for Nuclear Steam Generator Tubing", NDT&E International, 1994, 27(6):307-310.

Rose, J.L. et al., "Ultrasonic Guided Wave Inspection Concepts for Steam Generator Tubing", Materials Evaluation, 1994, pp. 307-311.

Rose, J.L., "Standing on the Shoulders of Giants: An Example of Guided Wave Inspection", Materials Evaluation, 2002, 60(1):53-59.

Rose, J.L., "Guided Wave Ultrasonic Pipe Inspection—The Next Generation", 8th European Conference on Non-Destructive Testing, Barcelona, Spain, Jun. 17-21, 2002 (IP) (RA-85), pp. 1-16.

Alleyne, D.N. et al., "Long Range Propagation of Lamb Waves in Chemical Plant Pipework", Materials Evaluation, 1997, pp. 504-508.

* cited by examiner

GUIDED WAVE PIPELINE INSPECTION SYSTEM WITH ENHANCED FOCUSING CAPABILITY

CROSS-REFERENCE TO RELATED APPLICATIONS

This U.S. non-provisional application claims the benefit of U.S. provisional patent application 60/867,976 filed Nov. 30, 2006, the entirety of which application is incorporated by reference in this application.

FIELD OF THE INVENTION

Aspects of the invention relate to pipeline inspection. More specifically, aspects of the invention relate to providing a guided wave pipeline inspection system with enhanced focusing capability.

BACKGROUND INFORMATION

Analysis of pipelines in-situ is an important function that, unfortunately, is not readily achievable with conventional technology. In order to investigate pipelines, such as for defects within the materials of the pipeline, the pipelines must be readily accessible for visual/material inspection. Pipelines that extend underground, therefore, must be uncovered so that investigators may visually identify the surface of the pipe.

Removal of the overburden from a pipe is a difficult and dangerous situation for work crews that are tasked with the function. To this end, the progress of analyzing pipelines is a costly proposition that also involves a safety concern of investigators. Pipelines that have changes in geometry, such as elbows, moreover, cannot be readily evaluated even by remote methods. Changes in geometry of a pipeline necessitate both direct visual inspection by inspectors and the ability to touch the pipeline in the area of concern so that material investigation can begin. Such access to the piping system may be impossible in certain circumstances, so these piping systems go uninspected. These significant drawbacks of conventional systems cost excessive money to be spent by pipeline owners who desire to carefully maintain their equipment to a desired standard.

In light of the drawbacks presented above, there is a need to provide for a pipeline inspection system that is mobile and is economical to use.

There is an additional need to provide a pipeline inspection system that can account for changes in geometry of the pipeline so that the pipeline may be remotely inspected.

There is an additional need to provide a pipeline inspection system that will account for various environmental and construction factors, such as a coating on a pipe.

There is a further need to provide a pipeline inspection system that will allow an investigator to pinpoint defects in a pipeline or analyze more closely a selected area of a pipeline desired by investigators.

SUMMARY

It is therefore an objective of an aspect of the present invention to provide for a pipeline inspection system that is mobile and is economical to use.

It is also an objective of an aspect of the invention to provide a pipeline inspection system that can account for changes in geometry of the pipeline so that the pipeline may be remotely inspected.

It is another objective of an aspect of the invention to provide a pipeline inspection system that will account for various environmental and construction factors, such as a coating on a pipe.

It is another objective of an aspect of the invention to provide a pipeline inspection system that will allow an investigator to pinpoint defects in a pipeline or analyze more closely a selected area of a pipeline desired by investigators.

It is also an objective of an aspect of the invention to provide a system that improves upon conventional technology wherein additional focal points are created around a circumference of a member to be evaluated without the need for additional pulsing and receiving equipment.

The objectives are achieved as illustrated and described. In an exemplary embodiment of the invention, a system for inspecting a pipeline, is presented comprising at least two transducers divided into segments, the segments each containing a number of sensors, wherein a maximum number of segments is equal to a number of transducers, an arrangement configured to send, receive and store signals, wherein the arrangement has a number of pulser channels and a number of receiver channels, wherein the arrangement has at least one multiplexing arrangement for multiplexing signals from the arrangement; and a time delay arrangement connected to the arrangement configured to send, receive and store signals, the time delay arrangement configured to calculate delay times for activation of the at least two transducers and activate the arrangement configured to send and receive signals for at least two transducers based upon the delay times.

In a further exemplary embodiment, the system may be configured such that at least two transducers are configured in a ring.

In a still further exemplary embodiment, a method for inspecting pipe having a change in geometry is presented. This method comprises the steps of creating a finite element model to simulate axisymmetricaly excited guided waves in the changed geometry pipe system, running the finite element model excited with the excited guided waves and obtaining results of the model, selecting a focus point on the model for focusing the guided waves, evaluating an approximate time delay for a phased array of transducers producing the guided waves to focus at the focus point, applying the approximate time delay for the phased array to focus at the focus point, running the finite element model with the approximate time delay for the phased array, evaluating results of the finite element model with the approximate time delay for the phased array, adjusting the time delay for the phased array based on the finite element model simulation results based on straight focusing, determining when guided waves based upon the adjusted time delay are focused at the focus point, adjusting the time delay when the energy is not focused at the focus point based on calculated straight pipe focusing coefficients, and deciding a final time delay for focusing beyond the change in geometry by comparing the time delay and a time delay for straight focusing and determining which focuses guided waves at the focus point.

In a further exemplary embodiment, the system may further comprise an arrangement to focus the phased array at locations other than a center of a segment.

In another exemplary embodiment, the system is configured such that the time delay arrangement is configured to calculate the time delay through a weight function.

In another exemplary embodiment, the system is configured such that the time delay arrangement is configured to calculate the weight function through a deconvolution of a partially loaded pressure profile of a single segment.

In another exemplary embodiment, the system is configured such that the arrangement configured to send, receive and store signals uses an algorithm that minimizes data collected from the pipe.

In a still further exemplary embodiment of the invention, the system is provided as in any embodiment above such that the algorithm uses a dominant displacement of particles in the pipe as a function of radius and angular position that is periodic as a function of axial distance in the pipe.

In another exemplary embodiment of the invention, the system is configured with a coating analysis arrangement configured to interface with the arrangement configured to send, receive and store signals, wherein the coating analysis arrangement is configured to calculate wave propagation change characteristics in the pipe based on a presence of a coating within the pipe. The coating analysis arrangement may allow for input of both a coating type and a coating thickness as well as the ability to generate an attenuation dispersion curve of the pipe.

DETAILED DESCRIPTION

Figure 3:
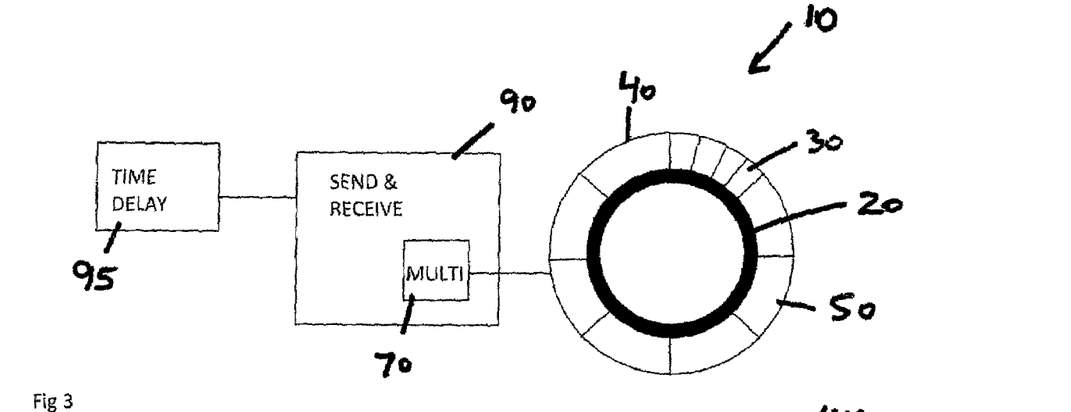
FIG. 3 is an arrangement drawing for a guided wave pipeline inspection system with enhanced focusing capabilities in accordance with an embodiment of the invention.
Figure 6:
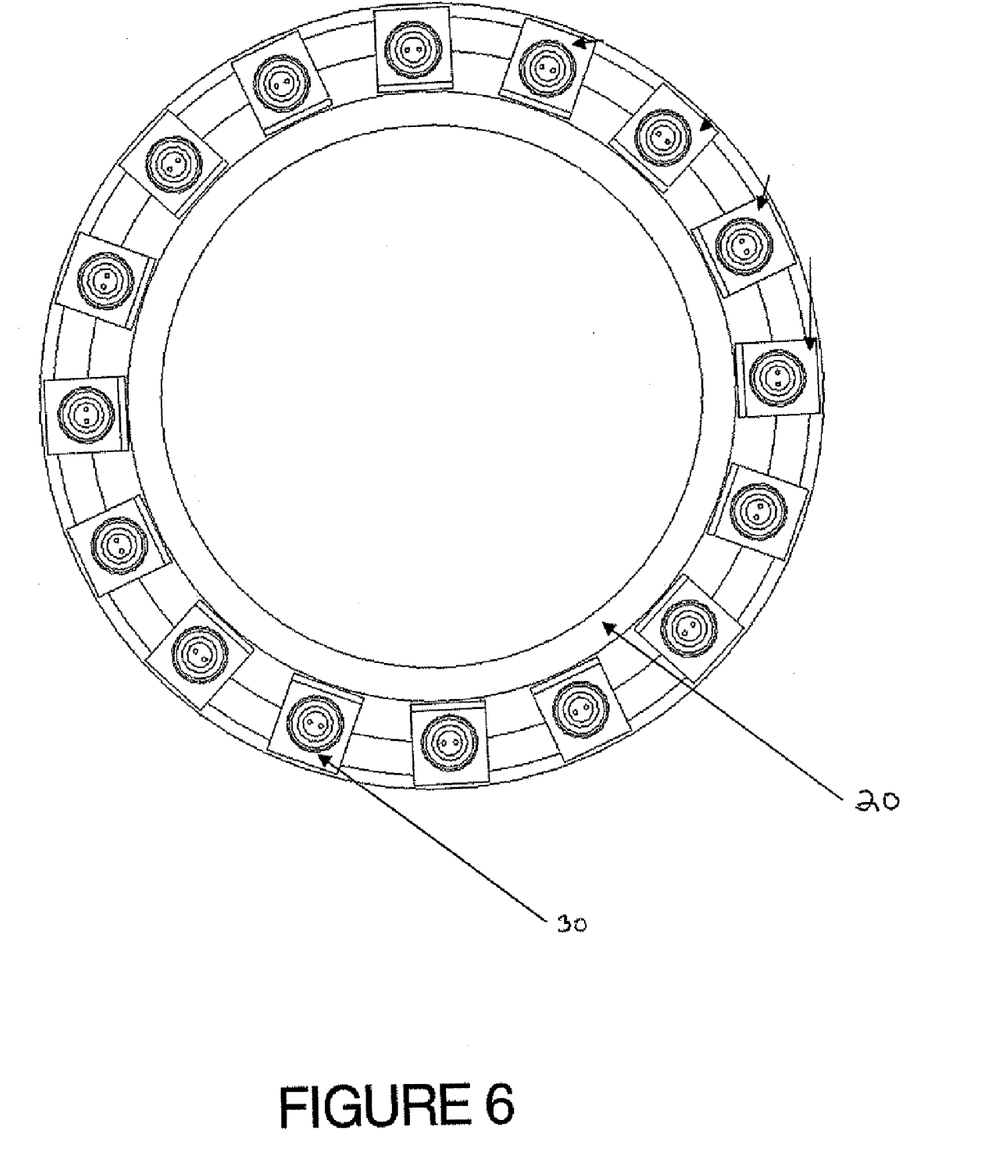
FIG. 6 is a front view of a transducer ring in conformance with the arrangement presented in FIG. 3.

Referring to FIG. 3, in an exemplary embodiment of the present invention, a system 10 for inspecting pipes 20 is presented wherein a number of transducers 30 are spaced around the circumference of the pipe 20. The transducers 30 may be in separate rings 40 placed around the pipe 20 for the purpose of unidirectional propagation or increased penetration power of guided wave signals. In the illustrated exemplary embodiment, only one ring of transducers 30 is present This exemplary embodiment does not limit the system 10 in any way to one ring. The same concept applies to systems with multiple transducer rings. Referring to FIG. 6, a sample ring 40 of transducers 30 is illustrated in further detail.

In the system 10, transducers 30 are divided into segments 50, each containing a finite number of sensors 60, with a maximum number of segments 50 being equal to the number of transducers 30. Each segment 50 is individually addressable. The system 10 then contains a finite number of pulser and receiver channels. Furthermore time delays can be input into each pulser and receiver channel. The time delays are used to focus the ultrasonic energy at a specific location in the pipe 20. The focal spot size can be changed by changing the number of transducers 30 in a segment 50.

An exemplary embodiment of the invention uses a finite number of channels to load up to 360° of the pipe 20, and multiplexes the channels into a finite number of segments. An arrangement 90 is also provided to send, receive and store signals, wherein the arrangement has a number of pulser channels and a number of receiver channels, wherein the arrangement 90 has at least one multiplexing arrangement 70 for multiplexing signals from the arrangement. By using the same number of channels with multiplexing, additional focal spots can be achieved along the pipe 20, including along areas where there is a change in geometry, such as a pipe elbow. This is done by focusing in each of the channel locations, then indexing the channels by one segment. A time delay arrangement 95 is connected to the arrangement configured to send, receive and store signals 90, the time delay arrangement 95 configured to calculate delay times for activation of the at least two transducers 30 and activate the arrangement configured to send and receive signals 90 for the least two transducers based upon the delay times.

When each time indexing occurs, a number of focal points equal to the number of channels is achieved and the focal points are shifted by the width of a segment 50. This process is repeated and indexing occurs until the original configuration is reached again. This will provide a number of focal points equal to the number of segments 50. In the instance where each segment 50 contains one transducer 30, the number of focal points will be equal to the number of transducers 30. Since multiplexing is more cost-effective than adding pulsing and receiving channels, a benefit is realized. The ability to have more focal locations at a given axial position is beneficial for circumferential sizing of defects as well as reflector characterization and analysis and depth or cross-sectional area sizing. Additionally, the embodiments of the present invention provide for obtaining focal points without affecting the focal zone, wherein the focal zone analyzed is sufficient to allow for determination of defects. This configuration prevents analysis results having large side lobes and missed calls due to focal point being too narrow.

As an example, a system with 8 channels and 64 sensors would normally have a total of eight focusing locations around the circumference at any axial position, as the segments would each have eight transducers. A system 10 with indexing could have up to 64 focal locations, if the segments each contained one sensor. If the segments each contain 2 sensors there will be 32 focal locations.

Figure 1:
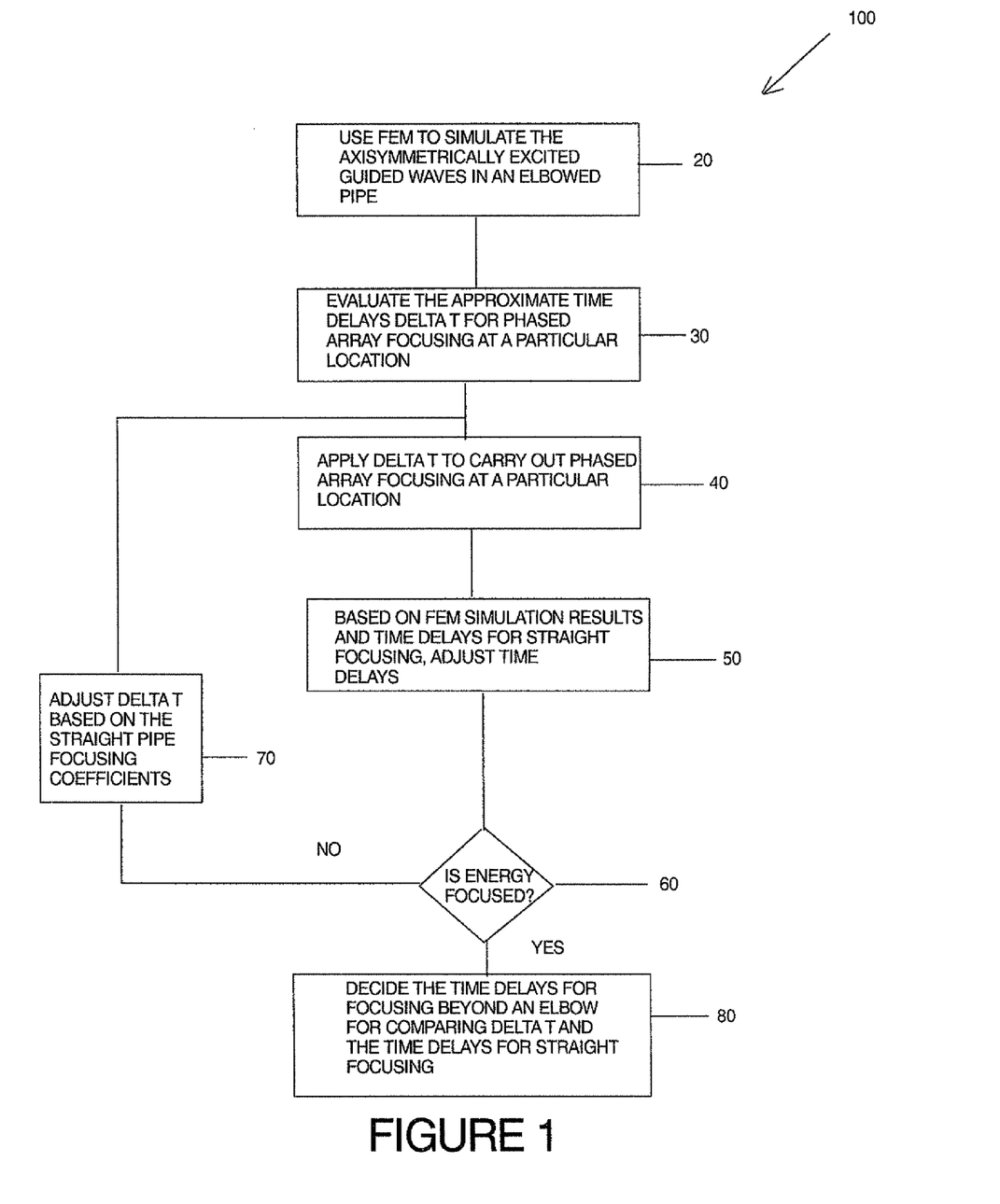
FIG. 1 is a flow chart of an algorithm for focusing a nondestructive examination beyond a geometry change, such as an elbow, in an exemplary embodiment of the invention.

In an additional exemplary embodiment of the present invention, an alternative system for inspecting pipes is presented. The system for inspecting pipes utilizes a specialized algorithm for focusing beyond geometry changes, such as, for example, elbows. The algorithm is a hybrid, finite element analytical approach. A flowchart of the process is presented in FIG. 1. Referring to FIG. 1, a method is provided for deciding time delays for focusing the guided waves for the arrangements provided 100. A finite element model is used to simulate the axisymmetrically excited guided waves in an elbowed pipe 20. Next, the approximate time delays (delta T) are evaluated for a phased array focusing at a particular location 30. The calculated (delta T) is applied to the phased array while focusing in the finite element model 40. Next, based on the finite element model simulation results and time delay for straight focusing, the time delays are adjusted 50. Next, it is determined if the energy focused is a the pre-selected position 60. If the energy is not focused at the pre-selected position, then the value of delta T is adjusted, based on the straight pipe focusing coefficients 70. If the energy is focused at the pre-selected position, then the time delays are decided for focusing beyond an elbow by comparing the delta T and the time delays for straight focusing 80.

In addition to this technique, the system 10 may also use a time reversal technique to focus sound energy at any point, including beyond an elbow. Time reversal is useful in the instances when there is a potential defect response present. Time reversal technique involves windowing the potential defect, reversing the response, and then using this signal as the pulse. Thus, this technique naturally focuses at the location where the response arrived from. If the response is a reflection from a defect, the signal will significantly increase in amplitude and if the signal is noise or another anomaly, the signal will not appreciably change.

In an alternative exemplary embodiment, a system for inspecting pipes is also presented that is capable of focusing through a phased array, to enable a focus at a position other than at the center of the segments. The exemplary system is capable of focal point skewing through the manipulation of time delays. The system is capable of focusing in a pipe, as provided in this exemplary embodiment, by using either a single or multiple ring of transducers. The rings are divided into segments which have individually addressable time delays in amplitude correction factors. These time delays in amplitude correction factors form a weight function that is calculated from a deconvolution of the partially loaded pressure profile for a single segment and a discrete function for an ideally focused profile. The non-symmetric time delay and amplitude factor are determined by the phase and amplitude of the single segment profile at the focal point. Furthermore, a continuation of this process is presented, whereby the discrete weight function is altered based on the focal location variation to skew the focal point. The focused profile will become more distorted as the focal point is moved further from the center of the segment; however, focusing is still achieved.

Figure 2:
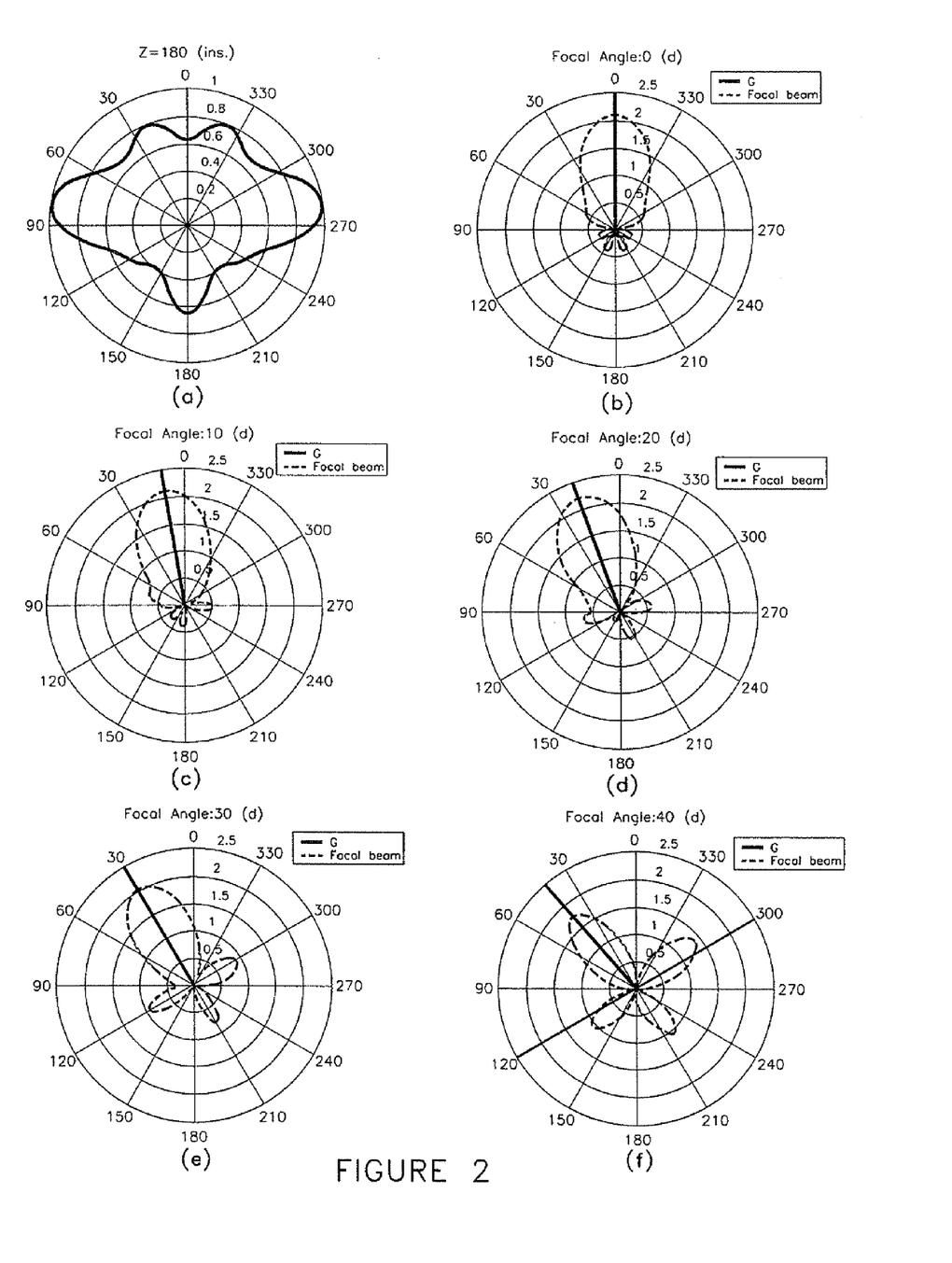
FIGS. 2A, 2B, 2C, 2D, 2E and 2F are sample angular profiles obtained by focusing a 35 kHz Torsional group on a 16 inch schedule 80 steel pipe.

Referring to FIG. 2A, an example is provided of a profile from a single partially loaded segment. FIG. 2B, is an example of an ideally focused profile with infinite numbers of channels and an actual focused profile with four channels, generated from the convolution of the partially loaded profile and weight function. A deconvolution of the ideal profile and the partially loaded profile produces a weight function with the time delays and amplitude correction factors for focusing. FIGS. 2C through 2F illustrate what happens as the weighting function is altered. The focal spot can also be skewed in the upper opposite direction by reversing the time delays. This technique allows the system to achieve more focal points around the circumference, with the same number of pulser and receiver channels. This is a benefit when sizing and locating a defect. No extra hardware is needed for locating such defects and improved circumferential resolution is achieved.

Figure 4:
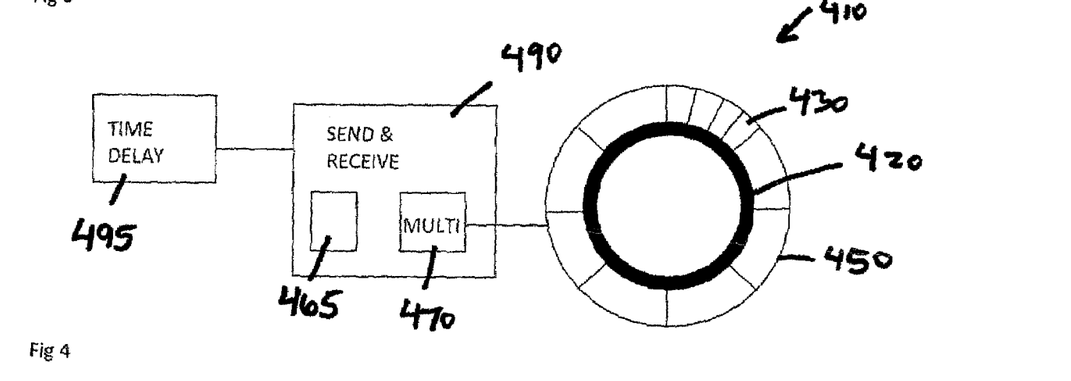
FIG. 4 is an arrangement drawing for a guided wave inspection system that uses a specialized algorithm for minimizing data obtained during inspection.

Referring to FIG. 4, in another exemplary embodiment of the invention, a system 410 for inspecting pipes 420 is presented wherein the system 410 utilizes a specialized algorithm in a processing unit 465 for focusing the guided waves imparted into the pipe 420. This specialized algorithm in the processing unit 465 reduces the amount of data collected. The reduction in data acquisition time leads to reduced inspection times, a significant improvement over conventional systems. In an exemplary embodiment of the invention, the algorithm is an equation that describes the dominant displacement of particles in the pipe as a function of radius and axial position and uses an angular position that is periodic as a function of axial distance of the pipe. Consequently, if time delays are entered into the system 410 to focus sound energy (i.e. ultrasonic energy) at a certain axial position, the sound may also be focused at several other axial positions in the pipe 420. Utilization of this concept drastically reduces the data collection time in a pipe 420. As an example, if for certain size pipe the partially loading profile repeats every 8 feet and the pipe is 80 feet long, 10 times less data would be required to inspect the entire pipe 420. This drastically reduces the time required for inspection. As provided in other embodiments of the invention, a time delay arrangement 495 may be connected to an arrangement configured to send/receive/store signals 490 for activation of transducers 450 that have segments 430. A multiplexing unit 470 may be used to multiplex the signals to the transducers to focus the energy to a desired point.

Figure 5:
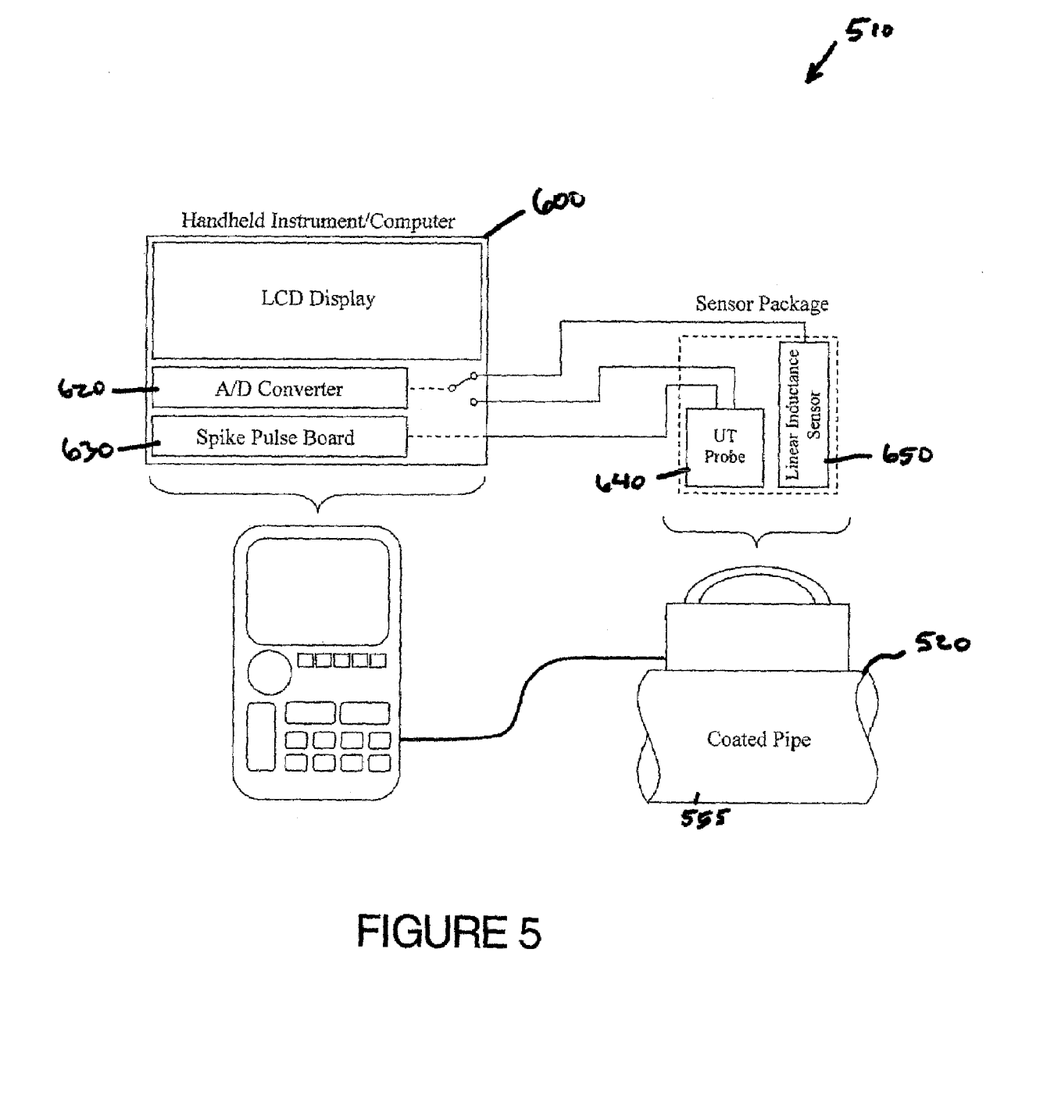
FIG. 5 is an arrangement drawing for a coating analysis system using guided wave technology.

Referring to FIG. 5, an alternative exemplary embodiment of the invention is provided using guided waves for analysis of pipes with coatings placed on the surfaces of the pipes. A coating analysis system 510 is presented to compensate for coatings 555 placed upon a pipe 520 in need of analysis. The system 510 may have a time delay compensation algorithm built into, for example, a handheld instrument/computer 600, that in turn has an LCD Display 610, an A/D Converter 620 and a Spike Pulse Board 630. The computer 600 is connected to a sensor package that has, in an exemplary embodiment, a UT probe 640 and a Linear Inductance sensor 650. When inspecting pipes, coatings are often encountered in many pipelines such as, bituminous or other viscoelastic coatings for corrosion protection. These coatings change the wave propagation characteristics of the pipe 520. Special tools are required to account for the changes caused by the coatings. By accounting for these changes, the best mode and frequency of excitation can be determined. This can increase penetration power. Penetration length can also be estimated for axisymmetric and focused loading. Also, corrections for coating effects can account for velocity changes. Velocity changes can affect location analysis and focusing algorithms, focusing time delay schedules must often be modified. This system 510 measures the coating properties and adjusts the time delay schedules for focusing. The system also compensates for temperature and other environmental conditions. Real time measurements are required for accurate adjustments and inspection length estimates.

What is claimed is:

1. A system for inspecting a pipeline, comprising:
at least two transducers radially disposed around a perimeter of the pipeline, each of the at least two transducers dividing the pipeline into segments, each segment containing a number of sensors, wherein a maximum number of segments is equal to a number of transducers;
an arrangement configured to send, receive and store guided wave signals along a length of the pipeline from a first location along the length of the pipeline, wherein the arrangement has a number of pulser channels and a number of receiver channels; and
a time delay arrangement connected to the arrangement configured to send, receive and store guided wave signals, the time delay arrangement configured to provide the arrangement configured to send and receive signals for at least two transducers with delay times for adjusting a radial position of the focal points or compensating for at least one of a geometric change or a coating along the length of the pipeline.

2. The system according to claim 1, wherein the at least two transducers are configured in a ring.

3. The system according to claim 1, further comprising:
an arrangement to focus a phased array at locations other than a center of a segment.

4. The system according to claim 3, further comprising:
applying at least one of non-symmetric time delays and amplitude controls to skew the focal point.

5. The system according to claim 4, where the time delay and an amplitude factor are determined by a phase and amplitude profile of a single segment at the focal point.

6. The system according to claim 1, wherein the arrangement configured to send, receive and store signals uses an algorithm that minimizes data collected from the pipe.

7. The system according to claim 1, further comprising:
a coating analysis arrangement configured to interface with the arrangement configured to send, receive and store guided wave signals, wherein the coating analysis arrangement is configured to calculate a wave propagation change characteristics in the pipe based on a presence of a coating within the pipe.

8. The system according to claim 6, wherein the algorithm accounts for advantage of periodicity that occurs as an acoustic wave travels down the pipe to decrease focusing time by focusing at multiple axial positions simultaneously.

9. The system according to claim 7, wherein the system coating analysis arrangement allows measuring acoustic properties of the coating.

10. The system according to claim 7, wherein the coating analysis arrangement is configured to generate an attenuation dispersion curve of the pipe.

11. The system according to claim 7, wherein a change in propagation characteristics is used to adjust at least one of the time delays and amplitude factors for focusing.

12. The system according to claim 1, wherein the arrangement is configured to use indexing to achieve focal points around a pipe circumference.

13. The system of claim 1, wherein the arrangement includes at least one multiplexing arrangement for multiplexing signals from the arrangement to provide a number of focal points at various locations around the perimeter of the pipeline, wherein the multiplexing arrangement is configured to increase the number of focal points by indexing the segment.

14. The system of claim 13, wherein a maximum increment is equal to the number of transducer segments.

* * * * *